US011608310B1

(12) United States Patent
Tan et al.

(10) Patent No.: US 11,608,310 B1
(45) Date of Patent: Mar. 21, 2023

(54) BIS(ANILINE) COMPOUNDS CONTAINING MULTIPLE SUBSTITUENTS WITH CARBON-CARBON TRIPLE-BONDED GROUPS

(71) Applicant: Government of the United States, as represented by the Secretary of the Air Force, Wright-Patterson AFB, OH (US)

(72) Inventors: Loon-Seng Tan, Centerville, OH (US); Zhenning Yu, Beavercreek, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 112 days.

(21) Appl. No.: 17/207,631

(22) Filed: Mar. 20, 2021

Related U.S. Application Data

(62) Division of application No. 16/752,772, filed on Jan. 27, 2020, now Pat. No. 10,988,437.

(60) Provisional application No. 62/908,168, filed on Sep. 30, 2019.

(51) Int. Cl.
*C07C 211/50* (2006.01)
*C07C 209/06* (2006.01)
*C07C 209/36* (2006.01)

(52) U.S. Cl.
CPC .......... *C07C 211/50* (2013.01); *C07C 209/06* (2013.01); *C07C 209/36* (2013.01)

(58) Field of Classification Search
None
See application file for complete search history.

(56) References Cited

U.S. PATENT DOCUMENTS

| | | |
|---|---|---|
| 4,045,409 A | 8/1977 | Arnold et al. |
| 5,606,014 A | 2/1997 | Connell et al. |
| 6,110,411 A | 8/2000 | Clausen et al. |
| 6,124,035 A | 9/2000 | Connell et al. |
| 6,350,817 B1 | 2/2002 | Connell et al. |
| 8,546,614 B1 | 10/2013 | Tan et al. |
| 8,668,981 B2 | 3/2014 | Karst et al. |

(Continued)

OTHER PUBLICATIONS

Connell, J. W.; Smith, J. G., Jr.; Hergenrother, P. M.: Oligomers and polymers containing phenylethynyl groups. Journal of Macromolecular Science, Reviews in Macromolecular Chemistry and Physics 2000, C40, 207-230.
Smith, J. G., Jr.; Connell, J. W.: Chemistry and properties of imide oligomers from phenylethynyl-containing diamines. High Performance Polymers 2000, 12, 213-223.

(Continued)

*Primary Examiner* — Sudhakar Katakam
*Assistant Examiner* — Jennifer C Sawyer
(74) *Attorney, Agent, or Firm* — AFMCLO/JAZ; James F. McBride

(57) ABSTRACT

The invention relates to bis(aniline) compounds containing multiple arylethynyl, alkylethynyl, ethynyl groups or their combinations, processes of making such compounds and materials comprising such compounds. Such, bis(aniline) compounds preferably comprise multiple phenylethynyl (PE) groups, i.e. 2-4 PE moieties. Such compounds are useful monomers for the preparation of polyimides, polyamides and poly(amide-imides) whose post-fabrication crosslinking chemistry (i.e. reaction temperature) can be controlled by the number of PE per repeat unit as well as finding utility in thermosetting matrix resins, 3D printable resins, and as high-carbon-content precursors to carbon-carbon composites.

1 Claim, 4 Drawing Sheets

(56) References Cited

U.S. PATENT DOCUMENTS

| | | |
|---|---|---|
| 8,791,227 B1 | 7/2014 | Tan et al. |
| 8,962,890 B1 | 2/2015 | Tan et al. |
| 10,239,254 B1 | 3/2019 | Tan et al. |
| 10,294,255 B1 | 5/2019 | Tan et al. |
| 10,480,098 B2 | 11/2019 | Ishihara et al. |
| 2010/0298323 A1 | 11/2010 | Bruncko et al. |
| 2015/0284498 A1 | 10/2015 | Weiss et al. |
| 2016/0369055 A1 | 12/2016 | Leng et al. |

OTHER PUBLICATIONS

Sastri, S. B.; Armistead, J. P.; Keller, T. M.; Carbonization of High-Temperature Resins, Carbon, 1993, 31, 4, 617-622.

Jones, K. M.; Keller, T. M.: Synthesis and characterization of multiple phenylethynylbenzenes via cross-coupling with activated palladium catalyst. Polymer 1995, 36, 187-92.

Smith, D. W., Jr.; Babb, D. A.; Snelgrove, R. V.; Townsend, P. H., III; Martin, S. J.: Polynaphthalene Networks from Bisphenols. Journal of the American Chemical Society 1998, 120, 9078-9079.

Fang, X.; Xie, X. Q.; Simone, C. D.; Stevens, M. P.; Scola, D. A.: A Solid-State 13C NMR Study of the Cure of 13C-Labeled Phenylethynyl End-Capped Polyimides. Macromolecules 2000, 33, 1671-1681.

Beringer, F. M.; Kravetz, L.; Topliss, G. B.: Iodonium Salts Containing Heterocyclic Iodine1-3. The Journal of Organic Chemistry 1965, 30, 1141-1148.

Kraszkiewicz, L.; Sosnowski, M.; Skulski, L.; Easy, inexpensive and effective oxidative iodination of deactivated arenes in sulfuric acid, Tetrahedron 2004, 60, 9113-9119.

Chen, J. C.; Wu, J. A.; Li, S. W.; Chou, S.C.: Highly phenylated polyimides containing 4,4'-diphenylether moiety. Reactive & Functional Polymers 2014, 78, 23-31.

Chen, J. C.; Wu, J. A.; Chang, H. W.; Lee, C. Y.: Organosoluble polyimides derived from asymmetric 2-substituted- and 2,2', 6-trisubstituted-4,4'-oxydianilines. Polymer International 2014, 63, 352-362.

Sastri, S. B.; Keller, T. M.; Jones, K. M.; Armistead, J. P.: Studies on cure chemistry of new acetylenic resins. Macromolecules 1993, 26, 6171-6174.

Chen, J. C.; Rajendran, K.; Chang, Y. H.; Huang, S. W.; Chern, Y. T.: Highly transparent and organosoluble polyimides derived from 2,2'-disubstituted-4,4'-oxydianilines. Journal of Applied Polymer Science 2011, 120, 3159-3170.

Chen, J. C.; Liu, Y. T.; Leu, C. M.; Liao, H. Y.; Lee, W. C.; Lee, T. M.: Synthesis and properties of organosoluble polyimides derived from 2,2'-dibromo- and 2,2',6,6'-tetrabromo-4,4'-oxydianilines. Journal of Applied Polymer Science 2010, 117, 1144-1155.

Grushin, V.V.; Cyclic diaryliodonium ions: old mysteries solved and new applications envisaged Chemical Society Reviews 2000, 29, 315-324.

Hu, B.; William H. Miller, W. H.; Kiel D. Neumann, K.D.; Linstad, E.J.; Dimagno, S.G.; An Alternative to the Sandmeyer Approach to Aryl Iodides Chem. Eur. J. 2015, 21, 6394-6398.

Donnell, J. W.; Smith, J. G., Jr.; Hergenrother, P. M.: Properties of imide oligomers containing pendent phenylethynyl groups High Performance Polymers 1997, 9, 309-321.

BIS(ANILINE) COMPOUNDS CONTAINING MULTIPLE SUBSTITUENTS WITH CARBON-CARBON TRIPLE-BONDED GROUPS

CROSS-REFERENCE TO RELATED APPLICATION

The present application is a divisional of and claims priority to U.S. patent application Ser. No. 16/752,772 filed Jan. 27, 2020, which in turn claims priority to U.S. Provisional Application Ser. No. 62/908,168 filed Sep. 30, 2019, both such priority applications being incorporated by reference herein as if fully set forth herein.

RIGHTS OF THE GOVERNMENT

The invention described herein may be manufactured and used by or for the Government of the United States for all governmental purposes without the payment of any royalty.

FIELD OF THE INVENTION

The invention relates to bis(aniline) compounds containing multiple acetylene and/or substituted acetylene groups, processes of making such compounds and materials comprising such compounds.

BACKGROUND OF THE INVENTION

Traditionally, bifunctional monomers are used in the creation of polyimides. In order to create polyimides, diamines are combined with dianhydrides so that the diamines may be joined to form a linear polyimide. When a non-linear or crosslinked polyimide is desired, at least a portion of the diamine is replaced with a triamine, or the dianhydride with a trianhydride. Unfortunately, when a triamine and/or trianhydride is employed, the crosslinking process typically occurs early in the reaction thus resulting in a non-processable product as the polyimide precursor becomes insoluble gel. In order to avoid the aforementioned solubility problem, post-polymerization crosslinkable endcaps are used. However, such endcapping presents additional issues as it cannot overcome the diametrically opposing relationship of the linear-segment molecular weight and crosslink density that are both critical to the processability and the final thermal-mechanical properties of the polyimide. Further solutions to such problem included the use of diamines that comprise two aromatic moieties and a "single-pendant post-polymerization crosslinkable" (SPC) moiety, wherein the amine functions are separate aromatic moieties from said single pendant post-polymer crosslinkable moiety. Unfortunately the crosslinking onset temperature of such SPC materials is not tunable.

Applicants recognized that the source of the aforementioned problems was due to the spatial difference in the crosslinkable moieties such as the SPC moiety. As a result of such recognition, Applicants produced a diamine comprising one to four crosslinkable moieties that have a conformation that puts said moieties during the polyimide production process in close spatial proximity. Thus, the aforementioned problems are reduced and significant processing flexibility is obtained.

SUMMARY OF THE INVENTION

The invention relates to bis(aniline) compounds containing multiple arylethynyl groups, processes of making such compounds and materials comprising such compounds. Such, bis(aniline) compounds comprise multiple phenylethynyl (PE) groups, i.e. 2-4 PE moieties. Such compounds are useful monomers for the preparation of polyimides, polyamides and poly(amide-imides) whose post-fabrication crosslinking chemistry (i.e. reaction temperature) can be controlled by the number of PE per repeat unit as well as finding utility in thermosetting matrix resins, 3D printable resins, and as high-carbon-content precursors to carbon-carbon composites.

BRIEF DESCRIPTION OF THE DRAWINGS

The accompanying drawings, which are incorporated in and constitute a part of this specification, illustrate embodiments of the invention and, together with the summary given above, and the detailed description given below, serve to explain the invention.

DETAILED DESCRIPTION OF THE INVENTION

Definitions

Figure 1:
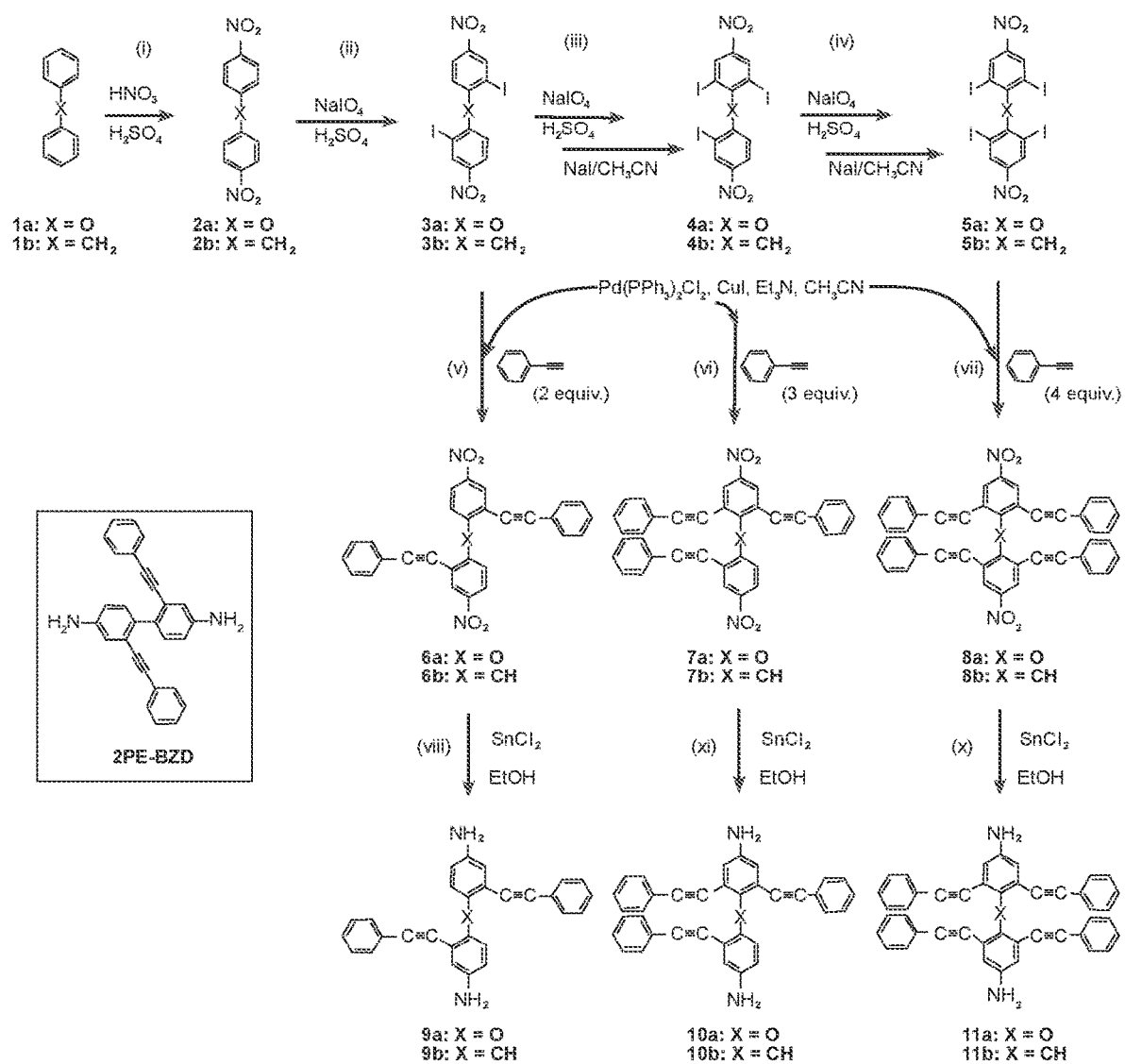
FIG. 1 depicts the synthesis of multiple phenyethynylated oxydianilines, methylenedianiline, and their respective bis(N,N'-phthalimide) derivatives. Inset depicts the structure for 2PE-BZD that contains two PE groups which are conjugatively linked across two phenylene rings.

Unless specifically stated otherwise, as used herein, the terms "a", "an" and "the" mean "at least one".

As used herein, the terms "include", "includes" and "including" are meant to be non-limiting.

As used herein, Ar can be a substituted or unsubstituted aromatic moiety

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Bis(Aniline) Compounds Comprising Multiple Substituents

For purposes of this specification, headings are not considered paragraphs and thus this paragraph is Paragraph 0018 of the present specification. The individual number of each paragraph above and below this paragraph can be determined by reference to this paragraph's number. In this paragraph, Applicants disclose a bis(aniline) compound having Structure 1 below:

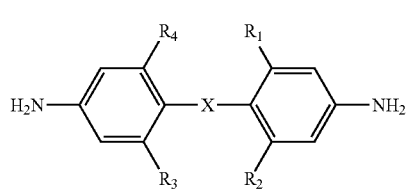

Structure I wherein
a) X is oxygen or $CH_2$, $R_1$ and $R_3$ are hydrogen and $R_2$ and $R_4$ are each $R_5C\equiv C$— wherein each $R_5$ is independently a hydrogen, an aryl moiety, an alkyl moiety; preferably $R_2$ and $R_4$ are each $ArC\equiv C$—;
b) X is oxygen or $CH_2$, $R_1$ is hydrogen and $R_2$, $R_3$ and $R_4$ are each $R_5C\equiv C$— wherein each $R_5$ is independently a hydrogen, an aryl moiety, an alkyl moiety; preferably $R_2$, $R_3$ and $R_4$ are each $ArC\equiv C$—; or
c) X is oxygen or $CH_2$, $R_1$, $R_2$, $R_3$ and $R_4$ are each $R_5C\equiv C$— wherein each $R_5$ is independently a hydrogen, an aryl moiety, an alkyl moiety; preferably $R_1$, $R_2$, $R_3$ and $R_4$ are each $ArC\equiv C$—.

As can be seen from Structure 1 above, said bis(aniline) compound can have multiple substituents containing ethynyl, alkylethnyl, arylethynyl or their combinations.

Applicants disclose the bis(aniline) compound of Paragraph 0018 wherein X is oxygen.

Applicants disclose the bis(aniline) compound of Paragraph 0019 wherein X is $CH_2$.

Applicants disclose the bis(aniline) compound of Paragraphs 0018 through 0020 wherein each Ar is independently phenyl, 1-naphthyl or 2-naphthyl.

Applicants disclose the bis(aniline) compound of Paragraphs 0018 through 0021 wherein at least one of $R_1$, $R_2$, $R_3$ and $R_4$ is 1-naphthalenylethynyl or 2-naphthalenylethynyl.

Applicants disclose the bis(aniline) compound of Paragraph 0021 wherein
a) $R_2$ and $R_4$ are each independently 1-naphthylethynyl or 2-naphthylethynyl;
b) $R_2$, $R_3$ and $R_4$ are each independently 1-naphthylethynyl or 2-naphthylethynyl; or
c) $R_1$, $R_2$, $R_3$ and $R_4$ are each independently 1-naphthylethynyl or 2-naphthylethynyl.

Applicants disclose that the bis(aniline) compounds of Paragraphs 0018 through 0023 may be multiple-arylethynylated bis(aniline) compounds.

The bis(aniline) compounds disclosed above are useful monomers in the preparation of polyimides, polyamides and poly(amide-imides) whose crosslinking chemistry (i.e. reaction temperature) can be controlled by the number of PE per repeat unit as well as finding utility in thermosetting matrix resins, 3D printable resins, and as high-carbon-content precursors to carbon-carbon composites. Such bis(aniline) compounds can be used to make: (a) high-temperature shape-memory polymers with a novel capability of continuous advancement in glass-transition temperature ($T_g$) and modulus during extended exposure to temperatures conducive to PE-PE reaction, i.e. $T_{rxn} \sim T_g + (50\text{-}100° C.)$ or 250-350° C.; and (b) to allow a latitude to select the curing temperature ($T_{curing}$) and processing window of phenylethynyl(PE)-based matrix resins. For (a), the shape-memory triggering temperature ($T_{trig}$) coincides with the initial glass-transition temperature ($T_g$,ini), and with cured-state glass-transition temperature, $T_{g,cured} \geq T_{trig} + 50°$ C. Uses of the disclosed bis(aniline) compounds include the fabrication of light weight aerospace structures and components, high-temperature resins or filaments for 3D printing, carbon-carbon composites, ablatives.

Processes of Making Bis(Aniline) Compounds Comprising Multiple Substituents

Applicants disclose a process of making a bis(aniline) compound comprising:
a) oxidatively halogenating Structure 2 below to form Structure 3 below wherein $R_1$ and $R_2$ are each independently I or Br, preferably $R_1$ and $R_2$ are I;
b) optionally, oxidatively iodinating chemical Structure 3 below one or two more times to form at least one of chemical Structures 4 through 5 below wherein $R_3$ and $R_4$ are each I:

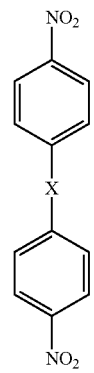

Structure 2

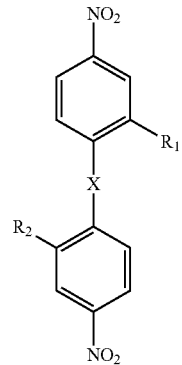

Structure 3

Structure 4

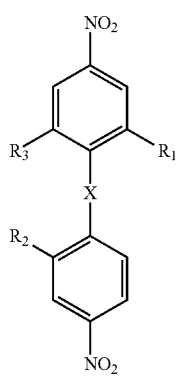

Structure 5

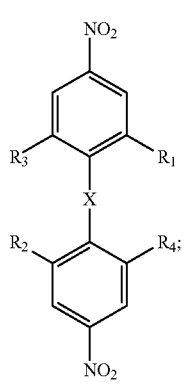

c) substituting the halogens on at least one of said chemical Structures 3 through chemical Structure 5 with a moiety comprising carbon-carbon triple bonded groups, preferably each of said moieties comprising said carbon-carbon triple bonded groups is independently acetylene or mono-substituted acetylene, preferably each mono-substituted acetylene is an aryl-substituted acetylene, preferably each aryl-substituted acetylene is independently phenylethynyl, 1-napthylethenyl or 2-napthylethynyl, to form at least one of chemical Structures 6 through 8 below, wherein $R_5$, $R_6$, $R_7$, and $R_8$ are each ethynyl moieties, preferably each $R_5$, $R_6$, $R_7$, and $R_8$ is an arylethynyl moiety, more preferably each $R_5$, $R_6$, $R_7$, and $R_8$ is independently phenylethynyl, 1-napthylethenyl or 2-napthylethynyl Structure 6

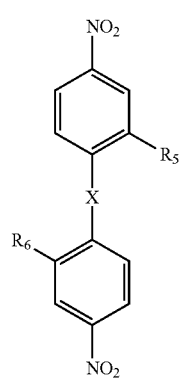

Structure 7

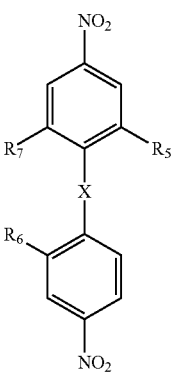

Structure 8

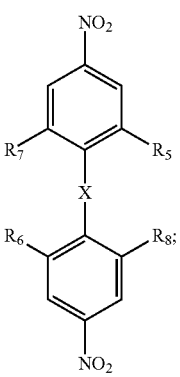

e) reducing the nitro moieties on at least one of said chemical Structures 6 through 8 to form at least one of chemical Structures 9, through chemical Structure 11 below:

Structure 9

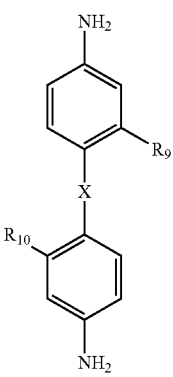

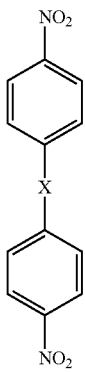

Structure 2

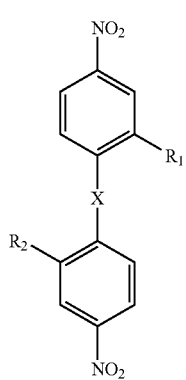

Structure 3

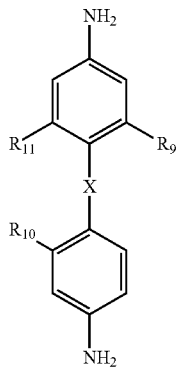

Structure 10

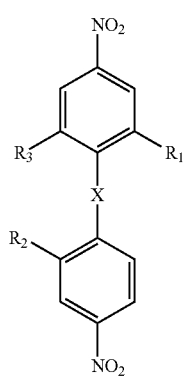

Structure 4

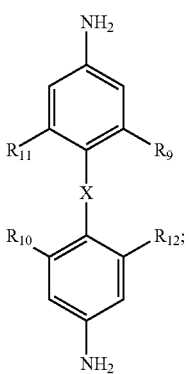

Structure 11

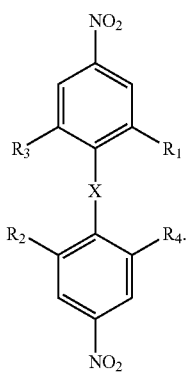

Structure 5 wherein $R_9$, $R_{10}$, $R_{11}$, and $R_{12}$ are a moiety comprising acetylene, preferably each of said moieties comprising acetylene is independently acetylene or mono substituted acetylene, preferably each mono-substituted acetylene is an aryl-substituted acetylene, preferably each aryl-substituted acetylene is independently phenylethynyl, 1-napthylethenyl or 2-napthylethynyl.

The process of Paragraph 0026 wherein said halogenating Structure 2 comprises oxidatively iodinating Structure 2 with a material comprising:
  a) a mixture formed by combining an iodide and an iodate and/or periodate in concentrated sulfuric acid preferably said iodide is NaI and/or KI and said iodate is $KIO_3$ and/or $NaIO_3$, or said iodide is NaI and/or KI and said periodate is $KIO_4$ and/or $NaIO_4$; and/or
  b) a mixture formed by combining I2 and $KIO_3$, $KIO_4$, $NaIO_3$ and/or $NaIO_4$ in concentrated sulfuric acid.

Applicants disclose a process according to Paragraphs 0026 through 0027 wherein said process comprises halogenating chemical Structure 2 below one or two more times to form chemical Structure 3, chemical structure 4 and/or chemical Structure 5 below wherein $R_3$ and $R_4$ are each I.

Applicants disclose the process of Paragraph 0028 comprising oxidizing Structure 3 with an oxidizing agent and then reducing said oxidized Structure 3 with a reducing agent comprising an iodide, optionally repeating said oxidizing and reducing processes.

Applicants disclose the process of Paragraph 0029 comprising repeating said oxidizing and reduction processes.

Applicants disclose the processes of Paragraphs 0029 through 0030 wherein said oxidizing agent is selected from the group consisting of the sodium or potassium salt of bromate, iodate, perbromate or periodate and said reducing agent is selected from the group consisting sodium iodide, potassium iodide and mixtures thereof.

Applicants disclose the processes of Paragraphs 0026 through 0031 wherein said process of reducing said nitro moieties comprises using a reducing agent selected from the group consisting of tin(II) chloride, Fe(II)/hydrazine, ammonium sulfide, sodium hydrosulfide and mixtures thereof. A milder reducing agent as provided herein is required at this point so that the triple bond found in $R_6$, $R_7$, $R_8$ and $R_9$ is not reduced.

Applicants disclose that processes of Paragraphs 0026 through 0032 can be used to produce multiple-arylethynylated bis(aniline) compounds.

Applicants recognized that as the properties of the precursor materials and the cured resins are influenced largely by molecular and microscale structures, the functionalization of oligomers or polymers with PE groups can be effected at the backbone, side chain or the termini. However, the thermally-induced reactivity of the PE groups depends not only on the location of the PE group in the oligomers or polymer molecule, but also depending on whether the precursors are in oligomeric or polymeric form, and whether in the solution or solid state. Broadly, the nature of reaction in polymeric solid can be categorized as either intramolecular (intra-chain) or intermolecular (inter-chain) mode. Below thermal degradation temperature and as dictated by the kinetic theory of molecular collision, temperature for "two-body" reaction ($T_{rxn}$) in solid state is usually lower at or above melting point ($T_m$) and in some cases that allow for molecular confinement of multiple reactive groups, $T_{rxn}$ can overlap with the glass-transition temperature ($T_g$). Furthermore, because of much higher effective concentration of PE groups in solid state than in solution, both intra- and inter-molecular reaction are more likely to occur concurrently unless that molecular confinement of multiple PE groups within the covalent-interaction distances is possible. In other words, the number density, proximity and associated effects of PE groups in an oligomeric (generally defined by having the number of repeating units of <10) or polymeric (generally defined by having the number of repeating units of >10) could be manipulated to control the $T_{rxn}$ with respect to $T_g$ or $T_m$), i.e. to control the processing windows for ($\Delta T = T_{rxn} - T_m$) PE-containing oligomers, and for property enhancement (e.g. $T_g$ & modulus) of PE-containing polymers ($\Delta T = T_{rxn} - T_g$). Experimental examples to illustrate the thermally-induced reactivity of multiple phenylethynylated compounds influenced by the relative positioning of multiple phenylethynyl groups on the same phenyl rings or two separated but linked phenyl rings as well as their associated thermal processing windows are provided in Table 1 below:

TABLE 1

The effects of PE Number density (PE/phenyl) and relative positioning (proximity) on the thermally-induced reactions (curing via various pathways radical polymerization intramolecular cyclization, intermolecular cycloaddition, crosslinking, etc. that can occur sequentially and/or concurrently.)

| Designation | Structure | $T_m$, (° C.)[a] | $T_{onset}$ (° C.)[a] | $T_{peak}$ (° C.)[a] | $\Delta$ ($T_{onset} - T_m$) |
|---|---|---|---|---|---|
| 135-3PE-Bz[a] | 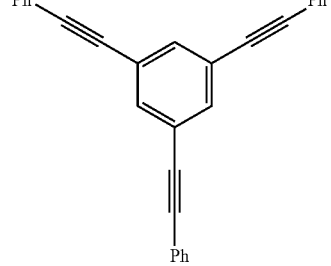 | 147 | 308 | 322 | 161 |
| 124-3PE-Bz[a] | 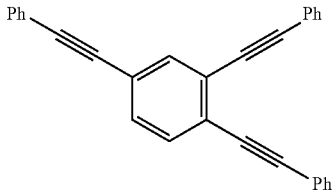 [SMILES: C(#Cc1ccc(C#Cc2ccccc2)c(C#Cc2ccccc2)c1)c1ccccc1] | 109 | 265 | 311 | 157 |
| 1245-3PE-Bz[b] | 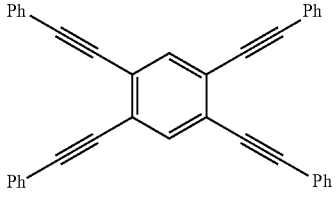 [SMILES: C(#Cc1cc(C#Cc2ccccc2)c(C#Cc2ccccc2)cc1C#Cc1ccccc1)c1ccccc1] | 195 | 251 | 291 | 56 |

TABLE 1-continued

The effects of PE Number density (PE/phenyl) and relative positioning (proximity) on the thermally-induced reactions (curing via various pathways radical polymerization intramolecular cyclization, intermolecular cycloaddition, crosslinking, etc. that can occur sequentially and/or concurrently.)

| Designation | Structure | $T_m$ (° C.)[a] | $T_{onset}$ (° C.)[a] | $T_{peak}$ (° C.)[a] | $\Delta (T_{onset} - T_m)$ |
|---|---|---|---|---|---|
| 4PE-ODA[c] | (structure: diphenyl ether with two phenylethynyl groups on each ring) | 108 | 205 | — | 97 |
| 2PE-BZD[d,e] | (structure: biphenyl diamine with two phenylethynyl groups) | 62 | 160<br>165[d] | 243<br>237-246[d] | 98 |

Notes:
[a] $T_m$ = melting point. $T_{onset}$ and $T_{peak}$ are the onset and peak temperatures, respectively of the reaction exotherms observed by DSC
[b] DSC values from S. B. Sastri el al. Macromolecules 1993, 26, 617 1-4;
[c] DSC values from D.W Smith, D, W
[d] DSC values from this work;
[e] DSC values for polyimides derived from 2PE-BZD and two bis( ether-phthalic anhydride) monomers as reported by Arnold, F E: Hedberg, F. L U.S. Pat. No. 4,045,400 (30 Aug. 1977)

Figure 2:
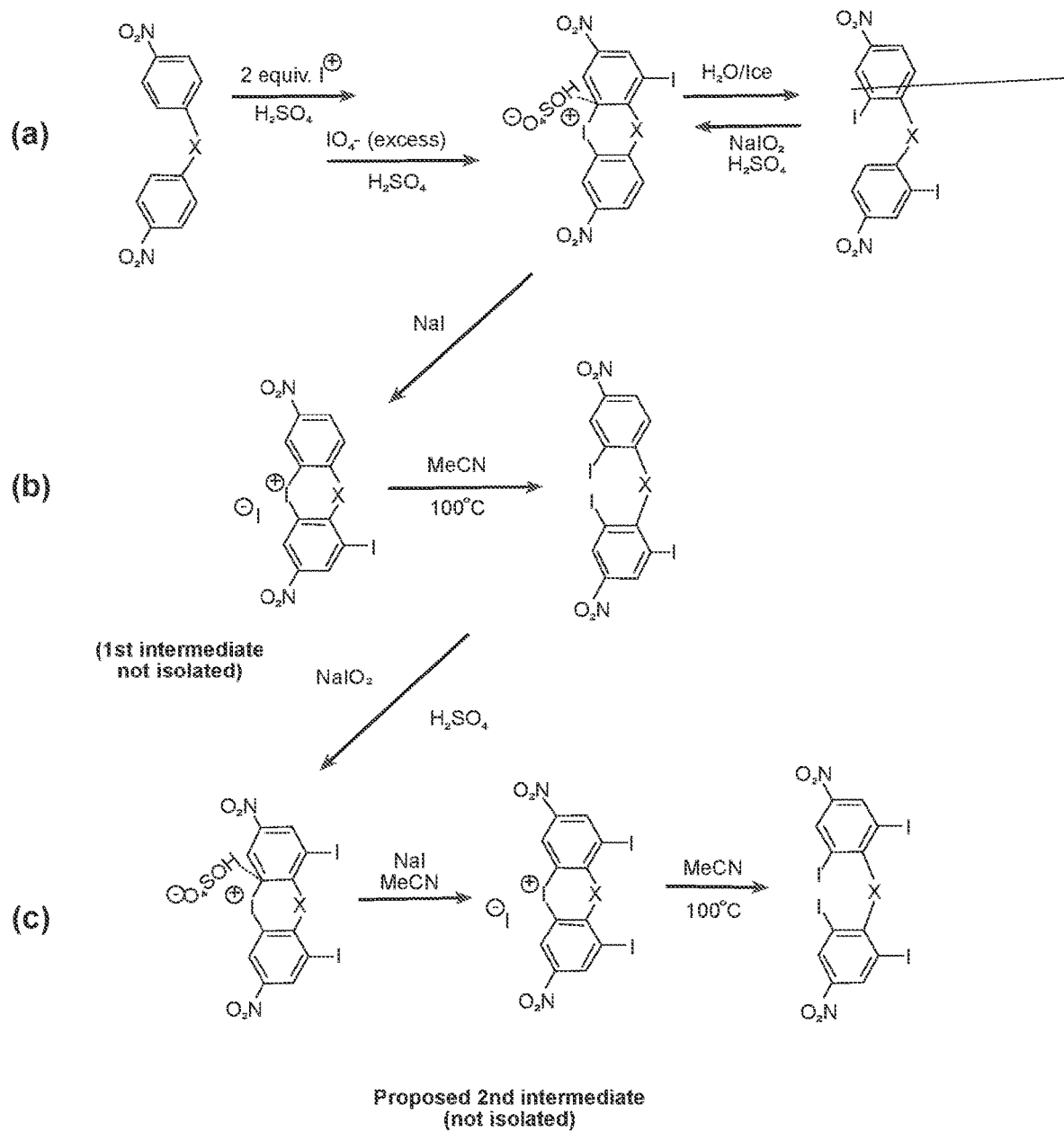
FIG. 2 depicts the syntheses of (a) di- (b) tri- and (c) tetra-iodobis(4-nitrobenzene). Sequence (a) is a one-pot oxidative iodination of the bis(4-nitrobenzene) starting materials followed by aqueous work-up to generate the corresponding di-iodo product. The synthesis of the triiodo-bis(4-nitrobenzene) compound entails step (a) to generate in-situ the first cyclic diaryliodonium iodide, which was then heated together with sodium iodide in acetonitrile, reaction (b), followed by aqueous work-up. Similarly, the synthesis of tetraiodo-bis(4-nitrobenzene) is conducted via the proposed intermediacy of the second cyclic diaryiodonium iodide after periodate oxidation and then the heating with NaI in $CH_3CN$, reaction (c).

Multi-phenylethynylated X-linked Diamine Synthesis: As depicted in FIG. 1, starting from diphenyl ether (1a) or diphenylmethane (1b), the general synthesis of multiple-phenylethynylated bis(aniline) compounds that are para-linked to a simple ortho- or para-directing X-group, namely either CH$_2$ or O are conducted using the following types of organic synthetic reactions: (a) nitration, step (i); (b) aromatic/oxidative iodination, steps (ii)-(iv); Cu/Pd-catalyzed aryl-ethynyl (Sonogashira) coupling reaction, steps (v)-(vi); (c) chemical reduction of nitro group. The key precursors to these diamines are the halogenated bis(4-nitrobenzene) compounds. The iodinated bis(4-nitrobenzene) compounds, 3a-b, 4a-b and 5a-b (FIG. 1) are preferred precursors in order to counter the steric hindrance inherent at the ortho positions during the Cu/Pd-catalyzed aryl-ethynyl coupling reaction because of the higher reactivity of aryl iodide than aryl bromide. In addition, because of the deactivation of the nitro groups in 2a-b, stronger oxidizing conditions using periodic acid (HIO$_4$) in addition to I$_2$ were required. As taught by L. Kraszkiewicz, et al. Synthesis 2006, 1195-1199, periodic acid is typically generated in situ by mixing the stable alkali (meta)periodate (e.g. NaIO$_4$) and concentrated sulfuric acid. When iodine (I$_2$) or iodide (from NaI or KI) is mixed with periodic acid in appropriate ratio (e.g. iodide:periodate=1:3), a strong electrophile, formally iodonium (I$^+$, that is capable to engage in electrophilic substitution reaction with even strongly deactivated arene (for example, by the presence of nitro group) is generated. This one-pot oxidative iodination procedure was applicable to the synthesis of the di-iodo-bis (4-nitrobenzene) compounds directly from the bis(4-nitrobenzene) starting materials. However, for the synthesis of tri- and tetra-iodo-bis(4-nitrobenzene) compounds, the one-pot procedure did not yield the desired products (see Comparative Examples 1 and 2). It has been known that diaryliodonium compounds (see V. V. Grushin, Chemical Society Reviews 2000, 29, 315-324) can be converted to aryl iodides efficiently using iodide salts under mild conditions (see B. Hu et al, Chemistry—A European Journal 2015, 21, 6394-6398.) Therefore, a two-step oxidative iodination involving the (i) isolation of the diaryiodonium intermediates, followed by (ii) the treatment with sodium iodide was used in this work (FIG. 2). In polar solvent such as acetonitrile, formally a tandem sequence of (ii-a) counter-ion exchange and (ii-b) aromatic nucleophilic substitution (ArS$_N$) at the ipso position by the iodide counter-anion. With the original aryliodonium moieity becoming aryliodide, the di-iodide arene product is resulted. Finally, in the aryl-ethynyl coupling reaction, there was an initial problem with Pd catalysis that resulted in mainly de-iodinated and cycloaddition side-products. The combined palladium-copper (Sonogashira) catalysis (in steps v-vii) helped to circumvent the problem. The final reaction (in steps vii-x, FIG. 1) requires the reduction of the two nitro groups in the presence of 2 phenylethynyl groups and the use of stannous chloride in ethanol as reducing system had worked out well.

Figure 3:
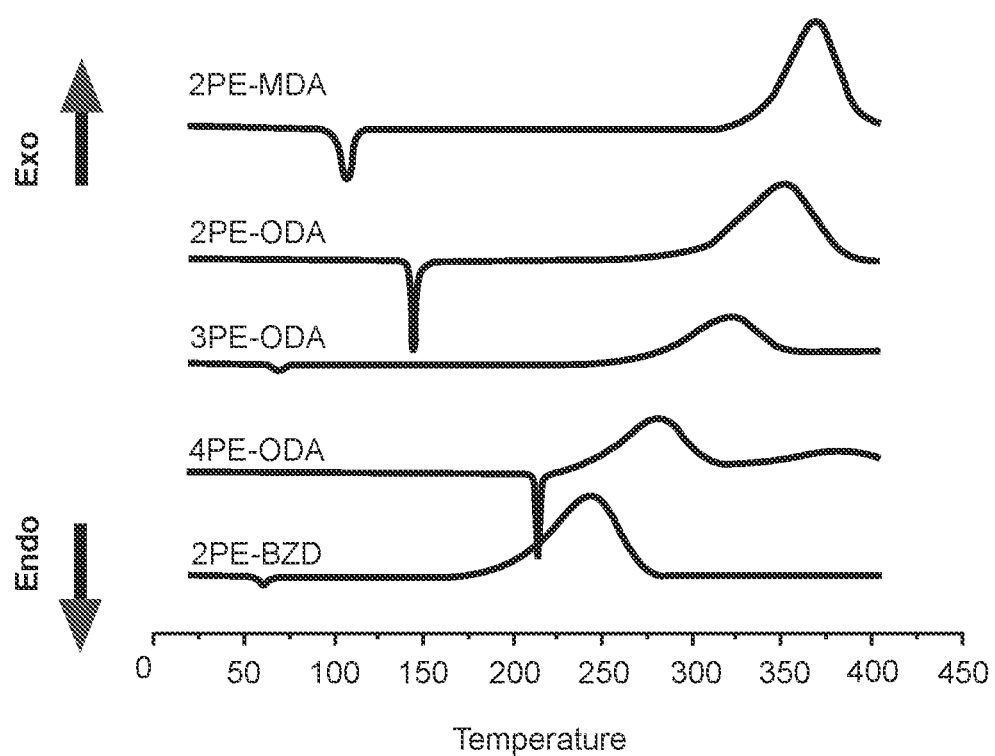
FIG. 3 provides DSC plots of multiple phenylethynylated methylenedianilines (2PE-MDA), oxydianilines (2PE-, 3PE- and 4PE-ODA) and benzidine (2PE-BZD), showing the temperature dependence of melting endotherm and thermal reaction exotherms on the PE number density and conjugation.
Figure 4:
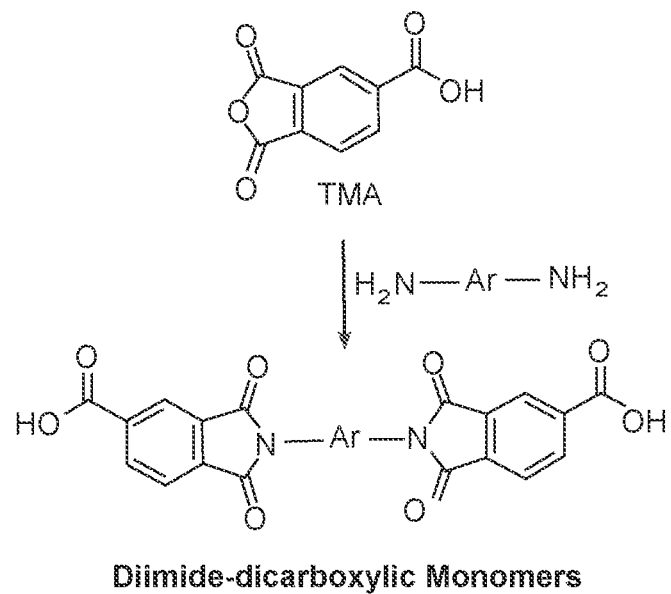
FIG. 4 depicts the synthesis of diimide-dicarboxylic and diamide-dianhydride monomers.
Figure 4:
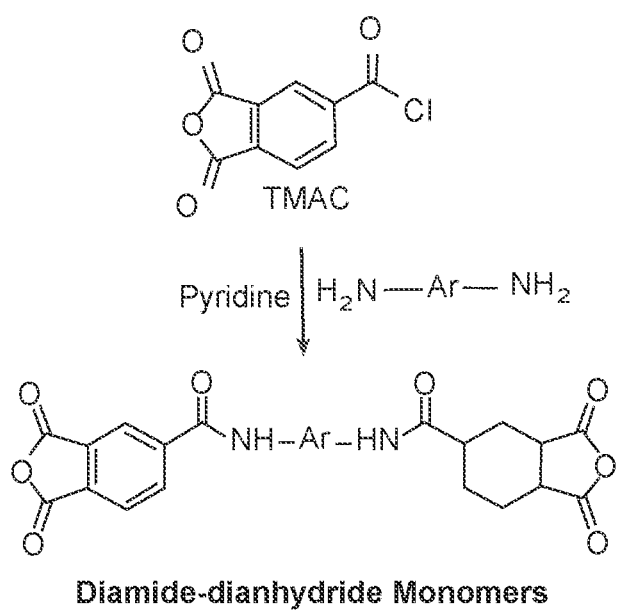

Thermal Properties: Thermal properties of the multiple phenylethynylated diamines were characterized by differential scanning calorimetry (DSC) that was conducted under nitrogen atmosphere, from 25° C. to 400° C., and at the scanning rate of 10° C./min. The composite DSC plots for 4,4'-oxybis(3-(phenylethynyl)aniline), 2PE-ODA (9a); 4,4'-methylenebis(3-(phenylethynyl)aniline), 2PE-DMA (9b); 4,4'-methylenebis(3-(phenylethynyl)aniline), 3PE-ODA (10a); 4,4'-oxybis(3,5-bis(phenylethynyl)aniline), 4PE-ODA (11a) and 2,2'-bis(phenylethynyl)benzidine, 2PE-BZD (FIG. 1 inset) are depicted in FIG. 3. Note that 2PE-BZD is included for comparison because of the conjugation and proximity of the PE groups located at two different benzene rings. This is in contrast to 2PE-ODA and 2PE-MDA whose two PE group are not conjugated because of the presence of an ether or a methylene separator, albeit still being in favorable proximity for a thermal pericyclic reaction due to the tetrahedral geometry of the ether oxygen and $CH_2$ units, hence angular linkages. However, the onset temperatures for 2PE-ODA, 3PE-ODA and 4PE-ODA are clearly higher than that for 2PE-BZD. The direct comparison of 2PE-ODA and 2PE-BZD suggests that conjugation effect lowers the reaction temperature and promote intramolecular pericyclic reaction. It is also noted that (i) within the MPA-ODA series, the trend for both the onset and peak temperatures is influenced by the number of PE moieties: 2PE>3PE>4PE; (ii) the occurrence of intermolecular reaction, i.e. crosslinking is likely as indicated by a smaller exotherm observed at temperatures >350° C. for 4PE-ODA. With respect to processing window for the respective PE materials that may be projected from the $\Delta(T_{onset}\text{-}T_m)$ in Table 2 below, 2PE- or 3PE-based materials are better than 4PE-based materials. However, because of the low $T_{onset}$ (221° C.), it may find uses as polymerization initiator for the phenylethynyl-terminated thermosetting oligomers that requires curing temperatures well above 350° C. Because of the similar polycondensation chemistry to generate polyimides, polyamides, and poly(amide-imides), the multiple phenylethynylated diamine compounds (FIG. 1) may be used as monomers or co-monomers for these polymers to create covalent network structures capable of showing shape memory effects at elevated temperatures.

TABLE 2

Thermal properties of multiple phenylethynylated diamines determined by DSC in $N_2$ at scanning rate of 10° C./min.

| Monomer | Mp (° C.) | $T_{onset}$ (° C.) | $T_{peak}$ (° C.) | $\Delta$ ($T_{onset}$ - $T_m$) (° C.) | Rxn Enthalpy (J/g) | Rxn Enthalpy (kJ/mol) |
|---|---|---|---|---|---|---|
| 2PE-BZD | 62.0 | 160 | 243 | 98 | 865 | 333 |
| 2PE-ODA (9a) | 145 | 238 | 352 | 93 | 746 | 299 |
| 2PE-MDA (9b) | 108 | 311 | 370 | 193 | 656 | 261 |
| 3PE-ODA (10a) | 71.0 | 238 | 321 | 167 | 500 | 250 |
| 4PE-ODA (10b) | 214 | 221 | 281 | 7 | 520 | 312 |

Crosslinked Polyimide Synthesis: The synthesis of a polyimide is typically accomplished by polymerization of a diamine and a dianhydride in a 1:1 molar ratio to generate a poly(amic acid) precursor, which is then converted to the corresponding polyimide typically by either thermal cure (heating to >200° C. in solution or solid state) or chemical imidization using a dehydrating agent or promoter such as acetic anhydride/triethylamine or acetic anhydride/pyridine. To generate a polyimide having the desired amount of crosslinking, an anhydride-terminated poly(amic acid) precursor is first generated by off-setting the dianhydride:diamine ratio so that the amount of diamine is in excess to cap both ends of linear poly(amic acid). An appropriate amount of a multifunctional anhhydride crosslinker is then added to the precursor solution so that all the anhydride endgroups will be consumed. Crosslinked polyimides may then be created using appropriate imidization conditions as above-described.

Crosslinked Polyamides Synthesis: The synthesis of a polyamide is typically accomplished by two general methods. The first method involves polymerization of a diamine and a diacid chloride in a 1:1 molar ratio in an amide solvent such as N,N-dimethylformamide (DMF), N,N-dimethylacetamide (DMAc), N-methylpyrrolidone (NMP), etc. To generate a polyamide having the desired amount of crosslinking, amine-terminated polymer is first generated by off-setting the diacid chloride:diamine ratio so that the amount of diamine is in excess to cap both ends of the polymer. Subsequent addition of a multifunctional anhydride crosslinker in appropriate amounts to the precursor solution so that all the amine endgroups are consumed, immediately followed by casting and thermal curing under reduced pressure, leads to the crosslinked polyamide films. The second method of synthesizing a polyamide involves polymerization of a diamine and a dicarboxylic acid with the aid of a promoter/catalyst combination such as triethylphosphite/pyridine (via Yamazaki-Higashi reaction), in an amide solvent such as N,N-dimethylformamide (DMF), N,N-dimethylacetamide (DMAc), N-methylpyrrolidone (NMP), etc. To generate a polyamide having the desired amount of crosslinking, a carboxylic acid-terminated polymer is first generated by off-setting the diacid:diamine ratio so that the amount of diacid monomer is in excess to cap both ends of the polymer. After the carboxylic acid-terminated polyamide into precipitated into water, it is washed (water & methanol) and dried. It is then redissolved in an amide solvent and mixed with an amide solution of a multifunctional amine crosslinker in appropriate amounts so that all the terminal carboxylic-acid groups are consumed, which is immediately followed by casting and thermal curing under reduced pressure to create crosslinked polyamide films.

Crosslinked Poly(amide-imide) Synthesis: The preparation of a poly(amide-imide) is typically accomplished by polymerization of (i) a diamine and a trimellitic anhydride (TMA) or trimellitic anhydride acid chloride (TMAC); (ii) a diamine and a diimide-dicarboxylic acid monomer derived from the selective condensation of trimellitic anhydride (TMA) and an aromatic diamine. When acid monomers are used, the polymerization process is aided by triethylphosphite/pyridine (Yamazaki-Higashi reagent) in a 1:1 molar ratio in amide solvents such as N,N-dimethylformamide (DMF), N,N-dimethylacetamide (DMAc), N-methylpyrrolidone (NMP) etc. For viable crosslinked poly(amide-imide) synthesis using trianhydride crosslinker instead of triamine crosslinker for which preparative routes (i) and (ii) are workable, a modification to (ii) would require specially designed bis(phthalic anhydride) monomers with preformed amide as part of the linking group. Such bis(phthalic anhydride) monomers, also known as diamidedianhydrides can be prepared from trimelltic anhydride acid chloride (TMAC) and an aromatic diamine in refluxing acetone with pyridine as HCl scavenger (Scheme 4).

To generate a poly(amide-imide) having the desired amount of crosslinking, an amine-terminatedprecursor polymer is first generated by off-setting the diamidedianhydride:diamine ratio so that the amount of diamine monomer is in excess to cap both ends of the polymer. Subsequent addition of a multifunctional anhydride crosslinker in appropriate amounts to the precursor solution so that all the amine endgroups are consumed, immediately followed by casting and thermal curing under reduced pressure, leads to the crosslinked (polyamide-imide) films. This method is in principle same as crosslinked polyimide synthesis via poly(amic acid) precursor as described above.

EXAMPLES

The following Examples 1-16 and methods are presented as illustrative of the present invention or methods of carrying out the invention, and are not restrictive or limiting of the scope of the invention in any manner. Examples 17 and 18 are comparative examples.

Example 1—Preparation of 2,2'-diiodo-4,4'-dinitrodiphenyl ether: To a 1 L three necked flask, equipped with a mechanical stirrer 95-98% sulfuric acid (400 mL) and sodium periodate (NaIO$_4$, 10.76 g; 50.5 mmol) were charged. To the suspension, potassium iodide (KI, 125.15 g, 51.5 mmol) was added within 1 hour. The mixture was stirred at room temperature for additional 1 hour. The resulting iodinating reagent was slowly added to a suspension of 4,4'-dinitrodiphenylether (26.02 g, 0.100 mol) in 200 mL of 95-98% sulfuric acid within one hour. The mixture was stirred for 3 hours, and poured into ice water in a large beaker. The precipitate was collected via filtration, washed several times with water, followed by 300 mL of ethanol, and finally air-dried with suction. The crude product was purified by recrystallization from toluene/heptane mixture. Two crops of crystals were harvested. 27.2 grams of crystals (53% yield) were obtained as the first crop of product, m.p. 171.6-174.6° C. Additional 10.7 grams of crystals (27.7% yield) were harvested as the second crop of product, m.p. 170.5-171.5° C. Total yield of the desired product is 37.9 g (81% purified yield). $^1$H-NMR (400 MHz, CDCl$_3$) δ=8.02-8.08 (d, J=4.8 Hz, 2H), 8.23-8.26 (dd, J=4.8, 8.8 Hz, 2H), 6.90-6.92 (d, J=8.8 Hz, 2H). Elemental analysis calculated for C$_{12}$H$_6$I$_2$N$_2$O$_5$, C %, 28.15; H %, 1.18; N %, 5.47; O %, 15.62. Found: C %, 28.06; H %, 1.14; N %, 5.16; O %, 15.78.

Example 2—Preparation of 2,2'-bis(phenylethynyl)-4,4'-dinitrodiphenylether. To a 500 mL round-bottomed flask, equipped with a stir bar, and nitrogen inlet, 2,2'-diiodo-4,4'-dinitrodiphenylether (25.60 g, 50.0 mmol), copper iodide (47.6 mg, 0.250 mmol) and bis(triphenylphosphine)palladium chloride (350.9 mg, 0.500 mmol) were charged. After three cycle of vacuuming and back-filling with nitrogen, phenylacetylene (20.43 g, 200 mmol), triethylamine (25 mL) and 100 mL of acetonitrile were added. The resulting mixture was stirred at room temperature for 4 hours, and then acetonitrile and excess phenylacetylene were removed under vacuum. Crude solids were washed with water, 90 mL of ethanol (3×), and air dried. The solids were dissolved in hot toluene, 2 grams activated carbon black was added, and the resulting mixture was then filtered. The product was further purified by recrystallization twice from toluene to give 15.38 grams of product as light yellow crystals, m.p. 180.5-181.9° C., in 66.7% yield. Additional 1.05 grams (m.p. 178.7-180.7° C., 4.6% additional isolated yield) was obtained as second crop of product. Total isolated yield is 16.43 (71%). $^1$H-NMR (400 MHz, CDCl$_3$) δ=8.49-8.50 (d, J=2.8 Hz, 2H), 8.18-8.21 (dd, J=2.8, 8.8 Hz, 2H), 7.30-7.42 (m, 10H), 7.09-7.11 (d, J=8.8 Hz, 2H). Elemental analysis calculated for C$_{28}$H$_{16}$N$_2$O$_5$, C %, 73.04; H %, 3.50; N %, 6.08; O %, 17.37. Found: C %, 73.03; H %, 3.47; N %, 6.20; O %, 17.33.

Example 3—Preparation of 4,4'-oxybis(3-(phenylethynyl)aniline) (2PE-ODA). To a 300 mL round bottom flask, equipped with nitrogen inlet, a stir bar, and a condenser, 2,2'-bis(phenylethynyl)-4,4'-dinitrodiphenylether (15.19 g, 30.00 mmol) and tin(II) chloride (44.66 g, 198.00 mmol) were charged. After three cycle of vacuuming and back-filling with nitrogen, 150 mL of ethanol was added. The resulting mixture was heated to 80° C., and held for 3 hours. After cooling to room temperature, the resulting reaction mixture was stripped off the ethanol solvent under vacuum, and the residue was treated with a solution comprised of 31.68 grams of sodium hydroxide in 620 mL water. The mixture was stirred for 30 minutes, and extracted with 200 mL of ethyl acetate (3×) by a separatory funnel. The combined organic solution was washed with de-ionized water three times, then dried over anhydrous sodium sulfate. The organic solution was filtered through a plug of silica gel, and then, concentrated under vacuum to give crude product as yellowish viscous oil. The oil was further purified by recrystallization three times from toluene. 4.18 g of final product was obtained as slightly yellow crystals, m.p. 141.7-142.7° C., 31.6% isolated yield. $^1$H-NMR (400 MHz, CDCl$_3$) δ=7.43-7.45 (m, 4H), 7.24-7.26 (m, 6H), 6.88 (d, J=2.8 Hz, 2H), 6.76-6.79 (d, J=8.8 Hz, 2H), 6.58-6.61 (dd, J=2.8, 8.8 Hz, 2H), 3.52 (brs, 4H). IR (cm$^{-1}$): 3433, 3412, 3355, 3330, 3211, 2208, 1607, 1496, 1480, 1435, 1261, 1218, 856, 818, 753, 687, 593, 531, 462. Elemental analysis calculated for C$_{28}$H$_{20}$N$_2$O: C %, 83.98; H %, 5.03; N %, 7.00; O %, 4.00. Found: C %, 83.63; H %, 4.98; N %, 6.95; O, 4.05. ESI-MS: m/z 401.2 [(M+H)$^+$].

Example 4—Preparation of 4,4'-dinitrodiphenymethane. To a 1000 mL three necked round bottom flask equipped with a stir bar and a thermometer, 102 mL concentrated sulfuric acid was added and cooled by ice-water bath. 70% Nitric acid (114 mL) was charged slowly. The mixture was cooled by ice-water bath to about 5° C. To the nitrating mixture, diphenylmethane (30.28 g, 0.18 mol) dissolved in 70 mL acetic acid was added at such a rate that the temperature is kept below 10° C. After addition of diphenylmethane/AcOH solution, the reaction mixture was stirred in an ice-water bath for 2 hours, and then poured into 600 g ice in a large beaker. The crude product was collected on a filter funnel, washed with de-ionized water (3×), ethanol (3×), times, and finally air dried. The crude product was purified by recrystallization from toluene to give near-white crystals. 15.82 grams of product was obtained, 34.0% isolated yield, m.p. 182.5-185.0° C. $^1$H-NMR (400 MHz, CDCl$_3$) δ=8.18 (d, J=8.5 Hz, 4H), 7.35 (d, J=8.4 Hz, 4H), 4.19 (s, 2H).

Example 5—Preparation of 2,2'-diiodo-4,4'-dinitrodiphenylmethane. To a 1000 mL round bottom flask equipped with a stir bar, 98% concentrated sulfuric acid (360 mL) and sodium periodate (NaIO$_4$, 9.68 g, 45.45 mmol) were charged. To the mixture, potassium iodide (KI, 22.63 g, 136.35 mmol) was added in small portion. After KI addition, the mixture was further stirred for half hour to form a dark brown solution. The resulting iodinating reagent in the form of the dark brown solution was added to a suspension of 4,4'-dinitrodiphenylmethane (23.24 g, 90.00 mmol) in 140 mL concentrated sulfuric acid over 5 hours. After addition, the reaction mixture was stirred at room temperature for additional 20 hours. The mixture was poured into 1000 g ice in a large beaker, and precipitated crude product was collected on a filter funnel. The crude solids were washed with copious amount of water, 5% aq. sodium bisulfite, water again, and finally air dried. The crude product was dissolved in ethyl acetate, and the insoluble particle was removed by filtration. The ethyl acetate filtrate was washed 3× with de-ionized water with the aid of a separatory funnel, and the dried over anhydrous sodium sulfate. After the removal of ethyl acetate by rotary evaporation, the crude product was obtained as slightly yellows solids. The crude product was further purified by recrystallization from toluene, to give 35.1 g product, m.p. 157.4-160.1° C., 76.4% isolated yield. $^1$H-NMR (400 MHz, CDCl$_3$): δ=8.74-8.75 (d, J=2.2 Hz, 2H), 8.15-8.17 (dd, J=8.4, 2.2 Hz, 2H), 7.07-7.09 (d, J=8.4 Hz, 2H), 4.31 (s, 2H). 13C NMR (101 MHz, CDCl$_3$): δ=148.3, 146.9, 134.6, 129.9, 123.5, 100.5, 51.8. IR (cm-1): 3102, 3091, 3071, 2848, 2450, 1893, 1796, 1595, 1564, 1457, 1342, 1243, 1142, 1116, 1033, 898, 846, 821, 741, 685, 658, 635, 417. Elemental analysis calculated for $C_{13}H_8I_2N_2O_4$, C %, 30.61; H %, 1.58; N %, 5.49; O %, 12.55. Found: C %, 30.63; H %, 1.54; N %, 5.36; O %, 12.59.

Example 6—Preparation of 2,2'-bis(phenylethynyl)-4,4'dinitrodiphenylmethane. To a 500 mL round bottom flask, equipped with a stir bar, and a nitrogen inlet, 2,2'-diiodo-4,4'-dinitrodiphenylmethane (35.70 g, 70.0 mmol), copper iodide (33.3 mg, 0.175 mmol) and bis(triphenylphosphine) palladium chloride (245.6 mg, 0.350 mmol) were charged. After three cycle of vacuuming and back-filling with nitrogen, phenylacetylene (28.56 g, 280 mmol), triethylamine (35 mL) and 140 mL acetonitrile were added. The mixture was stirred at room temperature for 4 hours, and then acetonitrile and excess phenylacetylene were removed under vacuum. Ethanol was added and the crude product was collected on a filter funnel, washed with 50 mL ethanol (6×), and then air dried. The crude solids were recrystallized from toluene to give 17.1 grams of product as light yellow crystals, m.p. 211.2-213.5° C., 53.3% isolated yield. $^1$H NMR (400 MHz, CDCl$_3$): δ=8.43 (d, J=2 Hz, 2H), 8.09-8.11 (dd, J=8.8, 2.0 Hz, 2H), 7.47-7.49 (d, J=6.8 Hz, 4H), 7.32-7.38 (m, 8H), 4.67 (s, 2H). Elemental analysis calculated for $C_{29}H_{18}N_2O_4$, C %, 75.97; H %, 3.96; N %, 6.11; O %, 13.96. Found: C %, 75.96; H %, 3.89; N %, 6.10; O %, 13.94.

Example 7—Preparation of 4,4'-methylenebis(3-(phenylethynyl)aniline) (2PE-MDA) To a 500 mL round bottom flask equipped with a stir bar, a condenser, and a nitrogen inlet, 2,2'-bis(phenyethynyl)-4,4'-dinitrodiphenylmethanel6.0 g (35.0 mmol), tin(ii) chloride (79.0, 0.35 mol) and 185 mL ethanol were charged. The mixture was heated in an oil bath temperature to 85° C. and held for 4 hours. After the mixture had been cooled to room temperature, ethanol was removed by rotary evaporation to give a viscous slurry. The slurry was poured into 550 mL of 10% potassium carbonate solution. The resulting mixture was filtered. The aqueous filtrate was extracted with 50 mL ethyl acetate for 3 times. The solid on the filter funnel was extracted with 200 mL ethyl acetate (5 times). The ethyl acetate extracts were combined, washed with 5% potassium carbonate solution followed by de-ionized water (2×), dried over sodium sulfate, and finally passed through a silica gel plug. After ethyl acetate had been removed on a rotary evaporator, the crude product was further purified by recrystallization from ethanol/water. 7.12 g of product was obtained as slight yellow needle like crystals, m.p 103.3-104.3° C., with a 51.5% isolated yield. $^1$H-NMR (400 MHz, CDCl$_3$): δ=7.44-7.46 (m, 4H), 7.25-7.26 (m, 6H), 6.95-6.97 (d, J=8.2 Hz, 2H), 6.85-6.86 (d, J=2.4 Hz, 2H), 6.53-6.55 (dd, J=8.2, 2.4 Hz, 2H), 4.30 (s, 2H), 3.53 (s, 4H). 13C NMR (101 MHz, CDCl$_3$): δ=144.2, 133.6, 131.5, 130.1, 128.2, 128.0, 123.5, 123.3, 118.2, 116.0, 92.7, 88.8, 36.6. IR (cm-1): 3424, 3402, 3207, 3053, 3022, 2207, 1607, 1570, 1500, 1489, 1442, 1324, 1071, 888, 840, 823, 753, 687, 608, 458. Elemental analysis calculated for $C_{29}H_{22}N_2$, C %, 87.41; H %, 5.56; N %, 7.03. Found: C %, 87.49; H %, 5.52; N %, 7.04. ESI-Ms: m/z 399.2 [(M+H)+]

Example 8—Preparation of 2,2',6-triiodo-4,4'-dinitrodiphenyl ether. To a 500 mL round bottom flask containing sodium periodate (NaIO$_4$, 4.28 g, 20.00 mmol) in 90 mL 98% concentrate sulfuric acid, sodium iodide (NaI, 8.99 g, 60.00 mmol) were added in small portions over 1 hours. After addition of sodium iodide, the mixture was future stirred for 1 hour. The resulting iodinating agent was then slowly added to a suspension of 4,4'-dinitrodiphenyl ether (10.41 g, 40.00 mmol) in 30 mL 98% concentrate sulfuric acid over a period of 1 hours. After addition, the mixture was stirred for additional 1 hour. More NaIO$_4$ (4.71 g; 22.00 mmol) was added to the mixture in small portions over 1 hour. After NaIO$_4$ addition, the mixture was stirred for another 2 hours, then poured over to 400 grams of ice in a large beaker. The precipitated crude product was collected by filtration, and washed with copious amount of water, followed by 5% aq. sodium bisulfite, de-ionized water, and finally acetone. After air drying, 20.6 grams yellow solids (cyclic iodonium bisulfate salt, not characterized) were obtained. To a 500 mL round bottom flask equipped with magnetic stir, and condenser, the above yellow product (cyclic iodonium bisulfate salt, sodium iodide, 20.6 g), sodium iodide (NaI, 22.80, 0.152 mol), and 200 mL of acetonitrile were charged. The mixture heated in an oil bath to 100° C., and held at that temperature for 6 hours. After the reaction mixture had been cooled to room temperature, acetonitrile was removed on a rotary evaporator and 300 mL of water was added to the residual solids, followed by extraction with by toluene (100 mL×4). The combined toluene extracts were washed with water, 5% aq. sodium bisulfite, de-ionized water, and finally dried over anhydrous sodium sulfate. After toluene had been removed on a rotary evaporator, the crude product was obtained and recrystallized from toluene/ethanol mixture to give light yellow crystals. After vacuum drying at 0.5 torr, 120° C. for 16 hours, 13.2 grams of product was obtained, m.p. 154.4-157.5° C., 51.7% isolated yield. $^1$H-NMR (400 MHz, CDCl$_3$): δ=8.77-8.32 (m, 3H), 8.11-8.14 (d, J=8.0 Hz, 1H), 6.33-6.35 (d, J=8.0 Hz, 1H). $^{13}$C-NMR (101 MHz, CDCl$_3$): δ=158.7, 158.2, 146.0, 143.7, 136.1, 135.4, 125.3, 112.7, 89.8, 85.4. IR (cm$^1$):3084, 3068, 2844, 2444, 1889, 1770, 1731, 1600, 1579, 1556, 1520, 1464, 1412, 1331, 1237, 1114, 1031, 900, 826, 736, 703, 651, 468, 425. Elemental analysis calculated for $C_{12}H_5I_3N_2O_5$, C %, 22.59; H %, 0.79; N %, 4.39; O %, 12.54. Found: C %, 25.39; H %, 1.18; N %, 4.03; O %, 12.30.

Example 9—Preparation of 2,2',6-tris(phenylethynyl)-4,4'-dinitrodiphenyl ether. To a 300 mL round-bottom flask equipped with a magnetic stir bar, a nitrogen inlet, 2,2',6-triiodo-4,4'-dinitrodiphenyl ether (6.38 g, 10 mmol), bis (triphenylphospine)palladium dichloride, (70.2 mg, 0.10 mmol), copper iodide (0.762 g (4.00 mmol) were charged. After three cycle of vacuuming and back-filling with nitrogen, 120 mL of acetonitrile was added. The mixture was stirred for 5 minutes before phenylacetylene (6.13 g, 60 mmol) and 30 mL of triethylamine were added. The mixture was stirred at room temperature for 16 hours, and the volatiles were removed from the reaction mixture by a rotary evaporator. The solid residues were washed with water, 5% aq. sodium carbonated solution and water again. After air drying, the crude product was dissolved in toluene, and solid impurities were removed by filtration. The toluene phase was washed with de-ionized water and dried over anhydrous sodium sulfate, concentrated under vacuum to give crude product. The crude product was purified by silica gel column chromatography, using toluene/heptane (2:3) as eluent and recrystallized from ethyl acetate/heptane mixture. 2.15 grams of product was obtained, m.p. 164.4-169.5° C., realizing a 38.3% isolated yield. $^1$H-NMR (400 MHz, CDCl$_3$): δ=8.49 (d, J=1.6 Hz, 1H), 8.40 (s, 2H), 8.08-8.10 (dd, J=2.0, 8.8 Hz, 1H), 7.49-7.51 (d, J=6.4 Hz, 2H), 7.26-7.35 (m, 13H), 6.83-6.85 (d, J=8.8 Hz, 1H). $^{13}$C-NMR (101 MHz, CDCl$_3$): δ=161.4, 159.2, 144.9, 143.0, 131.8, 129.6, 129.3, 129.2, 128.5, 127.8, 124.8, 122.2, 121.5, 119.7, 115.5, 114.8, 98.5, 97.1, 82.6, 81.9. Elemental analysis calculated for $C_{36}H_{20}N_2O_5$, C %, 77.14; H %, 3.60; N %, 5.00. Found: C %, 76.96; H %, 3.64; N %, 5.19.

Example 10—Preparation of 2,2',6-tris(phenylethynyl)-4,4'-diaminodiphenyl ether (3PE-ODA). To a 100 mL round bottom flask equipped with a condenser, a stir bar and a nitrogen inlet, 2,2',6-tris(phenylethynyl)-4,4'-dinitrodiphenyl ether (2.26 g, 4.00 mmol), stannous chloride dihydrate (9.03 g, 40.0 mmol) and 15 mL of ethanol were charged. The mixture was heated in an oil bath to the temperature set at 85° C. and held at that temperature for 3 hour. After the reaction mixture had been cooled to room temperature, 5 grams of sodium hydroxide in 40 mL ethanol was added and the final mixture was filtered. The solid residues were washed with 30 mL of ethanol (repeated 3×). The combined ethanol filtrate was concentrated on a rotary evaporator, and the residues were taken up in 100 mL toluene. The toluene phase was washed with 5% aq. potassium carbonate solution, distilled water, and dried over anhydrous sodium sulfate. After toluene had been removed from the filtrate, the crude product was obtained and purified by silica gel column chromatography, using ethyl acetate/heptane (2:3) as eluent. After chromatographic separation and rotary evaporation of ethyl acetate, the product was dissolved in ethanol, and precipitated in water. 0.82 grams of final product was obtained, as near light yellow solids, m.p. 77-83° C., 41% isolated yield. $^1$H-NMR (400 MHz, CDCl$_3$): δ=7.45-7.48 (m, 2H), 7.38-7.40 (m. 4H), 7.23-7.26 (m, 9H), 6,90 (d, J=2.0 Hz, 1H), 6.86 (s, 2H), 6.51-6.57 (m, 2H), 3.65 (brs, 2H), 3.43 (brs, 2H). $^{13}$C-NMR (101 MHz, CDCl$_3$): δ=152.7, 149.7, 142.9, 140.4, 131.7, 128.2, 128.0, 127.8, 123.8, 123.1, 119.5, 119.3, 119.0, 116.7, 115.7, 113.3, 94.2, 93.3, 86.4, 85.0. FT-IR (cm$^1$): 3446, 3360, 3215, 2213, 1616, 1590, 1491, 1443, 1433, 1293, 1221, 850, 753, 688. Elemental analysis calculated for $C_{36}H_{24}N_2O$, C %, 86.38; H %, 4.83; N %, 5.60; O %, 3.20. Found: C %, 86.48; H %, 4.89; N %, 5.91, 0%, 3.07.

Example 11—Preparation of 2,2',6,6'-tetraiodo-4,4'-dinitrodiphenyl ether. To a 300 mL round-bottomed flask containing 2,2',6-triiodo-4,4'-dinitrodiophen ether (16.52 g, 25.90 mmol), in 50 mL of 98% concentrated sulfuric acid, sodium perioidate (NaIO$_4$, 5.54 g, 25.9 mmol) were added in small portions over 1 hours. After NaIO$_4$ addition, the mixture was stirred for 16 hour, and poured over to 400 grams of ice in a large beaker. The precipitated "cyclic iodonium salt" intermediate was collected on a filter funnel, and washed with copious amount of water, followed by 5% aq. sodium bisulfite, de-ionized water, and finally acetone. After air drying, the "cyclic iodonium salt" crude was obtained as 16.9 grams of yellow solids. To a 500 mL round bottom flask equipped with magnetic stir, and condenser, the above product ("cyclic iodonium salt" crude (16.9 g), sodium iodide (NaI, 15.52 g, 0.104 mol) and 200 mL of acetonitrile were charged. The mixture heated in an oil bath to 100° C. and held at that temperature for 8 hours. After the reaction mixture had been cooled to room temperature, acetonitrile was removed form it on a rotary evaporator. 300 mL distilled water was added to the residues, which were extracted with toluene until thin layer chromatography indicated that there was no product in the toluene phase. The toluene extracts were combined and washed with water, 5% aq. sodium bisulfite, de-ionized water, and finally dried over anhydrous sodium sulfate. After removal of toluene from the extract on a rotary evaporator, the crude product was obtained and recrystallized from toluene mixture to give 7.8 grams of light yellow crystals, m.p 297.5-298.5° C., realizing a 39.4% isolated yield. $^1$H-NMR (400 MHz, CDCl$_3$): δ=8.71 (s, 2H). IR (cm$^{-1}$):3085, 3061, 2839, 1779, 1577, 1551, 1510, 1331, 1280, 1238, 1117, 1054, 8998, 740, 702, 686.

Example 12—Preparation of 2,2',6,6'-tetrakis(phenylethynyl)-4,4'-dinitrodiphenyl ether. To a 300 mL round bottom flask equipped with a magnetic stir bar and a nitrogen inlet, 2,2',66'-tetraiodo-4,4'-dinitrodiphenyl ether (3.82 g, 5.00 mmol), bis(triphenylphospine)palladium dichloride (70.1 mg, 0.10 mmol), copper iodide (0.190 g, 1.00 mmol) were charged. After three cycle of evacuating and back-filling with nitrogen, 120 mL of acetonitrile was added. The mixture was stirred for 5 minutes before phenylacetylene (6.13 g, 60 mmol) and 30 mL of triethylamine were added. The resulting mixture was stirred at room temperature for 48 hours. Crude product was obtained by filtration. The crude product was dissolved in hot toluene and filtered to remove some insoluble particles. To the hot toluene filtrate, ethanol was added, and the mixture was allowed to cool to room temperature on its own. The solid product formed in the EtOH/PhMe solution was collected on a filter funnel and washed with ethanol. 1.10 grams of product was obtained as yellow crystals, m.p. 237.9-240.9° C., realizing a 33.4% isolated yield. $^1$H-NMR (400 MHz, CDCl$_3$): δ=8.25 (s, 4H), 7.29-7.38 (m, 20H). Elemental analysis calculated for $C_{44}H_{24}N_2O_5$, C %, 79.99; H %, 3.66; N %, 4.24. Found: C %, 76.96; H %, 3.63; N %, 4.88.

Example 13—Preparation of 2,2',6,6'-tetrakis(phenylethynyl)-4,4'-diaminodiphenyl ether (4PE-ODA). To a 100 mL round bottomed flask equipped with a condenser, a stir bar and a nitrogen inlet, 2,2',6,6'-tetrakis(phenylethynyl)-4,4'-dinitrodiphenyl ether (1.65 g, 2.50 mmol), stannous chloride dihydrate (5.64 g, 25.0 mmol) and 15 mL of ethanol were charged. The mixture was heated in an oil bath to 85° C. and held at that temperature for 3 hour. After the reaction mixture had been cooled to room temperature, 2.0 grams of sodium hydroxide in 20 mL was added to the mixture. Solid crude was collected on a filter funnel (filtrate discarded) and washed with ethanol several times to extract the product into the filtrate. Ethanol was removed from the filtrate on a rotary evaporator, and 100 mL toluene was added to extract the solid residues. With the aid of a separatory funnel, the toluene phase was washed with 5% aq. potassium carbonate solution, distilled water, and finally dried with anhydrous sodium sulfate. The crude product was obtained after toluene was removed on a rotavap. The crude product was further purified by column chromatography, using ethyl acetate/heptane (2:3) as eluent. After chromatography the product was recrystallized from ethyl acetate/hexanes. 0.86 grams of the desired product was obtained as light yellow solids, m.p. 209.5-212.7° C., realizing a 57.3% isolated yield. $^1$H-NMR (400 MHz, CDCl$_3$): δ=7.38-7.40 (m, 8H), 7.23-7.24 (m, 12H), 6.69 (s, 4H), 3.42 (s, 4H). $^{13}$C-NMR (101 MHz, CDCl$_3$): δ=152.0, 141.4, 131.6, 128.0, 127.9, 123.4, 120.0, 116.3, 94.4, 85.6. IR (cm$^1$): 3342, 3363, 3078, 3053, 2202, 1615, 1592, 1489, 1441, 1224, 853, 753, 687, 531. Elemental analysis calculated for C$_{44}$H$_{28}$N$_2$O, C %, 87.98; H %, 4.70; N %, 4.66, 0%, 2.66. Found: C %, 87.92; H %, 4.71; N %, 4.81, 0%, 2.71

Example 14—Preparation of in-situ oxidative iodination reagent from iodine and sodium periodate. To a 1000 mL round bottom flask equipped with magnetic stir bar, 3.90 g (18.22 mmol) sodium periodate was slowly added into 350 mL of 95% sulfuric acid. Then, 13.88 g (54.69 mmol) iodine was added to the mixture slowly in 1 hours. After addition of iodine, the mixture was stirred at room temperature for 2 hours. The mixture as used as an oxidative iodination regents for 58 mmol of bis(4-nitrobenzene) in the same reaction vessel.

Example 15—Preparation of in-situ oxidative iodination reagent from sodium periodate and potassium iodide. To a 500 mL round bottom flask equipped with magnetic stir bar, 9.68 g (45.45 mmol) sodium periodate was slowly added into 360 mL of 95% sulfuric acid. Then, 22.63 g (136.35 mmol) potassium iodide was added to the mixture slowly in 1 hours. After addition of iodine, the mixture was stirred at room temperature for 1 hours. The mixture was used for oxidative iodination of 90 mmol of bis(4-nitrobenzene) in the same reaction vessel.

Example 16—Synthesis of 2,2',6-triiodo-4,4'-dinitrodiphenyl ether from 2,2'-diido-4,4'-dinitrodiphenyl ether via oxidation by sodium periodate and reduction by sodium iodide. To a suspension of 24.5 g (40.0 mmol) 2,2'-diido-4, 4'-dinitrodiphenyl ether in 130 mL concentrated sulfuric acid, 4.71 g (22.0 mmol) sodium periodate was added in small portion over one hours. After addition of sodium periodate, the mixture was stirred at room temperature for 1 hour, then poured into 400 grams of ice. Solids were collected by filtration, and washed with copious amount of water, 5% sodium bisulfite, de-ionized water, and finally 200 mL acetone. After air drying, 20.67 grams product was isolated as light yellow powder. 21.9 grams of yellow powder isolated from the above procedure, 22.80 grams (152.0 mmol) sodium iodide and 200 mL acetone was charged into 500 mL round bottomed flask equipped with magnetic stir bar and condenser. The mixture was heated to 100° C. and held for 8 hours. After the reaction mixture had been cooled to room temperature, acetonitrile was removed from it by vacuum, water was added to the residual solids, which were extracted by toluene. The toluene extracts were combined and washed with water, 5% sodium bisulfite, de-ionized water, and finally dried over anhydrous sodium sulfate. After toluene had been removed under vacuum, crude product was obtained. The crude product was recrystallized from toluene/ethanol mixture to give light yellow crystals. After vacuum drying at 0.5 torr, 120° C. for 16 hours, 13.4 grams of product was obtained, m.p. 154.2-158.2° C., 55.0% isolated yield.

Example 17 (Comparative)—Attempt to synthesis of 2,2', 6,6'-tetraiodo-4,4'-dinitrodiphenyl ether by one step oxidative iodination of 4,4'-dinitrodiphenyl ether. To a 300 three-necked round-bottomed flask, equipped with mechanical stir, 90 mL 98% sulfuric acid and 4.71 g (22.0 mmol) sodium periodate were charged. To the suspension, 9.89 g (66.0 mmol) sodium iodide was added within 1 hour. The mixture was stirred at room temperature for additional 1 hour. This mixture was slowly added to a suspension of 5.20 g (20.0 mmol) 4,4'-dinitrodiphenyl ether suspension in 30 mL 98% sulfuric acid within one hour. The mixture was stirred for 3 hours, then, poured into ice/water mixture. The precipitate was collected via filtration, washed several times with water, then 300 mL ethanol. 10.5 grams of product was obtained after air drying. The obtained product has a melting point>300° C. This product (10.5 g), sodium iodide 16.03 grams (107.0 mmol) and 100 mL acetone was charged into 300 mL round-bottomed flask equipped with a magnetic stir bar and a condenser. The mixture was heated to 100° C. and held for 8 hours. After the reaction mixture had been cooled to room temperature, acetonitrile was removed from it under vacuum. Water was added to the residual solids, which were extracted by toluene. The toluene extracts were combined and washed with water, 5% sodium bisulfite, de-ionized water, and finally dried over anhydrous sodium sulfate. After toluene had been removed under vacuum, the crude product was obtained, and recrystallized from toluene/ethanol mixture to give light yellow crystals. After vacuum drying at 0.5 torr, 120° C. for 16 hours, 5.35 grams of product was obtained, m.p. 154.5-158.5° C. The resultant product was confirmed by proton-NMR spectrum as 2,2',6-triiodo-4,4'-dinitrodiphenyl ether.

Example 18 (Comparative)—Attempt to synthesis of 2,2', 6,6'-tetraiodo-4,4'-dinitrodiphenyl ether by one step oxidative iodination of 2,2',6-triiodo-4,4'-dinitrodiphenyl. To a 50 mL round bottom flask, 10 mL of 98% sulfuric acid and sodium periodate (26.7 mg, 0.125 mmol) were charged. To the suspension, 56.2 mg (0.375 mmol) of sodium iodide was added within 1 hour. The mixture was stirred at room temperature for additional 1 hour. This mixture was slowly added to a suspension of 0.319 g (0.500 mmol) of 2,2',6-triodo-4,4'-dinitrodiphenyl ether suspension in 10 mL of 98% sulfuric acid within one hour. The mixture was stirred for 3 hours, then, poured into ice/water mixture. The precipitate was collected via filtration, washed several times with water. The isolated product was identified as starting material based on proton NMR spectrum.

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

What is claimed is:

1. A process of making multiple-arylethynylated bis(aniline) compound comprising:
   a) oxidatively halogenating Structure 2 below to form Structure 3 below wherein R$_1$ and R$_2$ are each I and X is oxygen or CH$_2$;
   b) optionally, oxidatively iodinating chemical Structure 3 below one or two more times to form at least one of chemical Structures 4 through 5 below wherein R$_3$ and R$_4$ are each I:

Structure 2

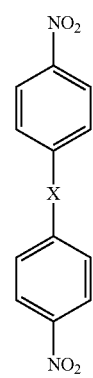

Structure 3

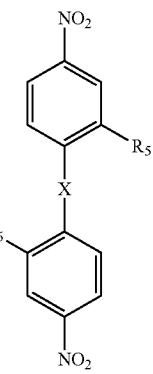

Structure 4

Structure 5 through 8 below, wherein $R_5$, $R_6$, $R_7$, and $R_8$ are each independently phenylethynyl, 1-naphthylethynyl or 2-naphthylethynyl Structure 6

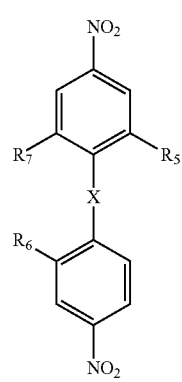

Structure 7

Structure 8 c) substituting the halogens on at least one of said chemical Structures 3 through chemical Structure 5 with phenylethynyl, 1-naphthylethynyl or 2-naphthyl-ethynyl, to form at least one of chemical Structures 6 e) reducing the nitro moieties on at least one of said chemical Structures 6 through 8 to form at least one of chemical Structures 9, through chemical Structure 11 below:

Structure 9
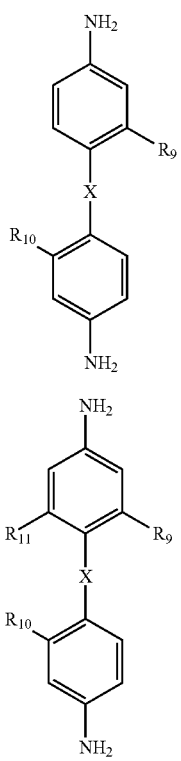
Structure 10
Structure 11
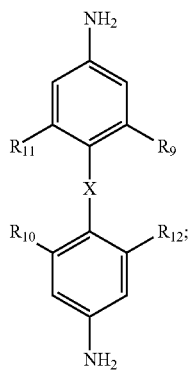
wherein $R_9$, $R_{10}$, $R_{11}$, and $R_{12}$ are each independently phenylethynyl, 1-naphthylethynyl or 2-naphthylethynyl.
* * * * *